US010026507B2

(12) United States Patent
Cho et al.

(10) Patent No.: US 10,026,507 B2
(45) Date of Patent: Jul. 17, 2018

(54) APPARATUS AND METHOD FOR MANAGING A CARE SERVICE

(71) Applicant: LG CNS CO., LTD., Seoul (KR)

(72) Inventors: Chun-Rae Cho, Seoul (KR); Jeong Pyo Kim, Seoul (KR); Sung Yong Park, Seoul (KR); Soon Gi Yoon, Seoul (KR); Kwan Pyo Lee, Seoul (KR); Moon Ho Ha, Seoul (KR); Sung Ho Kim, Seoul (KR)

(73) Assignee: LG CNS CO., LTD., Seoul (KR)

( * ) Notice: Subject to any disclaimer, the term of this patent is extended or adjusted under 35 U.S.C. 154(b) by 455 days.

(21) Appl. No.: 14/300,067

(22) Filed: Jun. 9, 2014

(65) Prior Publication Data

US 2015/0356256 A1 Dec. 10, 2015

(51) Int. Cl.
*G16H 40/20* (2018.01)
*G06Q 50/22* (2018.01)
*G06F 19/00* (2018.01)

(52) U.S. Cl.
CPC ............ *G16H 40/20* (2018.01); *G06F 19/00* (2013.01); *G06Q 50/22* (2013.01); *G06Q 2220/00* (2013.01)

(58) Field of Classification Search
CPC ..... G06F 19/322–19/327; G06Q 50/22–50/24; G06Q 2220/00; G16H 40/20
See application file for complete search history.

(56) References Cited

U.S. PATENT DOCUMENTS

| 2009/0210712 A1* | 8/2009 | Fort | H04L 63/1441 713/175 |
| 2009/0245029 A1* | 10/2009 | Kam | G06K 19/07 368/10 |
| 2013/0086201 A1* | 4/2013 | Legge | G06Q 10/10 709/217 |
| 2013/0232082 A1* | 9/2013 | Krawczewicz | G06F 19/323 705/55 |

FOREIGN PATENT DOCUMENTS

| JP | 2001-273368 A | 10/2001 |
| JP | 2008-257699 A | 10/2008 |
| JP | 2012-243318 A | 12/2012 |

* cited by examiner

*Primary Examiner* — Sheetal R Paulson

(57) ABSTRACT

A method manages a care service by a terminal apparatus of a caregiver. The method includes recognizing a smart card of a patient, receiving encrypted data including encrypted time information from the smart card, the encrypted time information being generated at the smart card by encrypting time information corresponding to a point in time when the terminal apparatus recognizes the smart card, and transmitting the encrypted data to a management server. The encrypted data is generated by the smart card using an encryption key and decrypted by the management server using a decryption key corresponding to the encryption key. A time corresponding to time information acquired from the decrypted data is stored in the management server as a care service providing time.

18 Claims, 12 Drawing Sheets

FIG. 9

| Total | 10 | Complete | 1 | Not Served | 9 | In Served | 0 | Alert | 0 |

Period: [01/15/2014] ~ [01/16/2014] [By Recipient] [ALL ▼] 🔍 Search

| Date | Sch Start | Sch End | Sch Hrs | Recipient(920) | Attendant(930) | Check in(940) | Check Out(950) | Act Hrs | Type | Status |
|---|---|---|---|---|---|---|---|---|---|---|
| 01/15/2014 | 01:00 | 22:00 | 21:00 | John Doe | Sara Kim | | | | | Not Served |
| 01/15/2014 | 07:00 | 08:00 | 01:00 | Lala Kim | Adam Scott | | | | | Not Served |
| 01/15/2014 | 09:00 | 10:00 | 01:00 | Adam cho | Sara Kim | | | | | Not Served |
| 01/15/2014 | 12:00 | 13:00 | 01:00 | Lala Kim | Adam Scott | | | | | Not Served |
| 01/15/2014 | 18:00 | 19:00 | 01:00 | Adam cho | Adam Scott | | | | | Not Served |
| 01/15/2014 | 18:41 | 18:41 | 00:00 | Adam cho | Tommy Lee | | | | | Not Served |
| 01/15/2014 | 19:00 | 20:00 | 01:00 | John Doe | Adam Scott | | | | | Not Served |
| 01/16/2014 | 09:00 | 10:00 | 01:00 | Adam cho | Sara Kim | 10:26 | 10:28 | 00:02 | Telephony | Completed |
| 01/16/2014 | 18:00 | 19:00 | 01:00 | Adam cho | Adam Scott | | | | | Not Served |
| 01/16/2014 | 19:00 | 20:00 | 01:00 | Adam cho | Adam Scott | | | | | Not Served |

Showing 1 to 10 of 10 entries

First | Previous | 1 | Next | Last

APPARATUS AND METHOD FOR MANAGING A CARE SERVICE

TECHNICAL FIELD

Embodiments of the present disclosure relates to an apparatus and method for managing a care service. More particularly, embodiments of the present disclosure relates to an apparatus and method for managing a home-care service for a patient.

BACKGROUND

Home-care services are provided to patients who reside in houses or sanatoriums. A caregiver who is employed by a service provider visits a patient in person, and provides the patient with a care service suitable for the patient, such as nursing, therapy, bathing, dressing, preparation of meals, grocery shopping, ordering prescription, laundry, escort services on medical visits, and other personal care services.

Home-care services are provided based on a public medical insurance system or a private medical insurance system. Therefore, a designated caregiver visits a patient assigned to the designated caregiver at an appointed time and provides a scheduled service to the patient.

In a conventional method for managing a care service, a care service start time and a care service end time for a patient are managed through documentation. This may imposed excessive burden of work on caregivers.

Moreover, when a mobile terminal is used in the related art to manage care services, when a caregiver visits a patient while holding the terminal, a position of the terminal is checked using a global positioning system (GPS), and the terminal determines a time of arrival at a patient's location as a care service start time, and determines a time at which the terminal departs from the patient's location by at least a predetermined distance as a care service end time. However, such a method has a drawback in that the terminal of the caregiver and a server managing the terminal should always be connected through a network. That is, if the terminal and the management server are not connected through a network, the management server cannot recognize where the terminal apparatus is. Consequently, it is difficult to determine exactly the care service start time and the care service end time.

Furthermore, according to the conventional methods, a caregiver may deliberately falsify a care service start time and a care service end time.

SUMMARY

Various embodiments are directed to a system and method for managing a care service. Embodiments are also directed to a terminal apparatus, a management server, and a smart card, which manage a care service providing time at which a caregiver provides a care service to a patient even when the terminal apparatus and the management server are not connected through a network.

Embodiments are directed to a system and method for managing a care service, and a terminal apparatus, a management server, and a smart card, which prevent a caregiver from falsifying a care service providing time.

In accordance with an embodiment, a method manages a care service by a terminal apparatus of a caregiver, the method including: recognizing a smart card of a patient; receiving encrypted data including encrypted time information from the smart card, the encrypted time information being generated at the smart card by encrypting time information corresponding to a point in time when the terminal apparatus recognizes the smart card; and transmitting the encrypted data to a management server.

The method further includes generating and transmitting unencrypted time information to the smart card.

The method may further include: receiving identification information of the smart card from the smart card; comparing the identification information of the smart card with identification information of smart cards of patients assigned to the caregiver; determining whether the patient is assigned to the caregiver based on a result of the comparison; and transmitting the encrypted data to the management server if it is determined that the patient is assigned to the caregiver.

The method may further include outputting information on the patients assigned to the caregiver if it is determined that the patient is not assigned to the caregiver.

The encrypted data may generated by the smart card using an encryption key and decrypted by the management server using a decryption key corresponding to the encryption key.

When the time information is first time information that is generated when the smart card is first recognized by the terminal apparatus, and the encrypted data is first encrypted data including encrypted first time information, the method may further include: recognizing the smart card a second time; receiving second encrypted data including encrypted second time information from the smart card, the encrypted second time information being generated by the smart card by encrypting second time information corresponding to a point in time when the terminal apparatus recognizes the smart card the second time; and transmitting the second encrypted data to a management server. The management server may store a care service start time and a care service end time based on the first encrypted data and the second encrypted data, respectively.

The method may further include determining a present time so as to acquire the time information.

The method may further include outputting information on a care service to be provided to the patient if it is determined that the patient is assigned to the caregiver.

The method may further include outputting an alarm message if the smart card is not recognized within a predetermined time interval from a visit reservation time for the patient.

The method may further include: receiving care schedule data from the management server; and receiving a push message indicating a change of a care schedule, which corresponds to the care schedule data, from the management server if the care schedule is changed after the terminal apparatus has received the care schedule data.

The method may further include: receiving condition information of the patient; and transmitting the condition information to the management server.

The method may further include: receiving biometric information of the caregiver; and authenticating the caregiver using the biometric information.

Transmitting the encrypted data may include: determining whether the terminal apparatus can connect to the management server through a network; if it is determined that the terminal apparatus can connect to the management server through the network, transmitting the encrypted data to the management server; if it is determined that the terminal apparatus cannot connect to the management server through the network, storing the encrypted data; re-determining whether the terminal apparatus can connect to the management server after a predetermined time elapses; and if it is determined that the terminal apparatus can connect to the management server through the network, transmitting the stored encrypted data to the management server.

In accordance with another embodiment, a method manages a care service by a management server, the method including: receiving encrypted data including encrypted time information from a terminal apparatus of a caregiver, the encrypted time information being obtained by encrypting, at a smart card of a patient, time information corresponding to a point in time when the smart card is recognized by the terminal apparatus; decrypting the encrypted data to acquire the time information; and storing a time related to a care service for the patient based on the time information.

When the encrypted data further includes identification information of the smart card, and the method may further include: receiving identification information of the terminal apparatus from the terminal apparatus; and determining whether a patient corresponding to the identification information of the smart card is assigned to a caregiver corresponding to the identification information of the terminal apparatus.

When the encrypted data further includes a hash value generated by the smart card, the method may further include determining whether the encrypted data is falsified based on a hash value generated by decrypting the encrypted data.

The method may further include: receiving, from the terminal apparatus, biometric information of a person in possession of the terminal apparatus and identification information of the terminal apparatus; comparing the biometric information received from the terminal apparatus with biometric information included in the identification information of the terminal apparatus; determining whether the biometric information from the terminal apparatus matches with the biometric information corresponding to the identification information of the terminal apparatus; and if it is determined that the biometric information does not match, storing information indicating that the care service for the patient has not been normally performed.

When the time information is first time information that is generated when the smart card is first recognized by the terminal apparatus, and the encrypted data is first encrypted data including encrypted first time information, the method may further include: receiving second encrypted data including encrypted second time information from the terminal apparatus, the encrypted second time information being obtained by encrypting, at the smart card, the second time information corresponding to a point in time when the smart card is recognized a second time by the terminal apparatus; decrypting the second encrypted data to acquire the second time information; and storing a time related to the care service for the patient based on the second time information. The management server may store a care service start time and a care service end time based on the first time information and the second time information, respectively.

The method may further include: receiving identification information of the terminal apparatus and a care schedule request from the terminal apparatus; and transmitting, to the terminal apparatus, care schedule data of patients assigned to the caregiver corresponding to the identification information of the terminal apparatus.

The method may further include transmitting a push message indicating a change of a care schedule, which corresponds to the care schedule data, to the terminal apparatus if the care schedule is changed after the care schedule data has been transmitted to the terminal apparatus.

In accordance with still another embodiment, a terminal apparatus of a caregiver includes: a card recognizer configured to recognize a smart card of a patient; a memory having stored therein instructions; and a processor being controlled by the instructions and performing a method, the method including: receiving encrypted data including encrypted time information from the smart card, the encrypted time information being generated at the smart card by encrypting time information corresponding to a point in time when recognizing the smart card; and transmitting the encrypted data to a management server.

The time information may be generated in the terminal apparatus and transmitted to the smart card.

The method of the terminal apparatus may further include: receiving identification information of the smart card from the smart card; comparing the identification information of the smart card with identification information of smart cards of patients assigned to the caregiver; determining whether the patient is assigned to the caregiver based on a result of the comparison; and transmitting the encrypted data to the management server if it is determined that the patient is assigned to the caregiver.

The method of the terminal apparatus may further include: outputting information on the patients assigned to the caregiver if it is determined that the patient is not assigned to the caregiver.

When the time information is first time information that is generated when the smart card is first recognized by the terminal apparatus, and the encrypted data is first encrypted data including encrypted first time information, if the card recognizer recognizes the smart card a second time, the method of the terminal apparatus may further include: receiving second encrypted data including encrypted second time information from the smart card, the encrypted second time information being generated at the smart card by encrypting second time information corresponding to a point in time when the smart card is recognized the second time; and transmitting the second encrypted data to the management server. The management server may store a care service start time and a care service end time based on the first encrypted data and the second encrypted data, respectively.

The method of the terminal apparatus may further include: determining a time corresponding the time information.

The method of the terminal apparatus may further include: receiving identification information of the smart card from the smart card; and outputting information on a care service to be provided to a patient corresponding to the identification information of the smart card.

The method of the terminal apparatus may further include: outputting an alarm message when the smart card is not recognized within a predetermined time interval from a visit reservation time for the patient.

The method of the terminal apparatus may further include: receiving care schedule data from the management server; and receiving a push message indicating a change of a care schedule corresponding to the care schedule data from the management server if the care schedule is changed after the care schedule data has been received.

The method of the terminal apparatus may further include: receiving condition information of the patient, and transmitting the condition information to the management server.

The method of the terminal apparatus may further include: receiving biometric information of the caregiver; and authenticating the caregiver using the biometric information.

The method of the terminal apparatus may further include: determining whether the terminal apparatus can connect to the management server through a network; transmitting the encrypted data to the management server if it is determined that the terminal apparatus is connected to the management server through the network; storing the encrypted data if it is determined that the terminal apparatus cannot connect to the management server; determining again whether the terminal apparatus can connect to the management server after a predetermined time elapses; and transmitting the stored encrypted data to the management server if the terminal apparatus is connected to the management server.

In accordance with further still another embodiment, a management server for managing a care service for a patient, the management server including: a memory having stored therein instructions; a processor being controlled by the instructions and performing a method, the method including: receiving encrypted data including encrypted time information from a terminal apparatus of a caregiver, the encrypted time information being obtained by encrypting, at a smart card of the patient, time information corresponding to a point in time when the smart card is recognized by the terminal apparatus; and decrypting the encrypted data to acquire the time information; and a storage circuit configured to store a time related to the care service for the patient based on the time information.

When the encrypted data further includes identification information of the smart card, the method of the management server may further include: receiving identification information of the terminal apparatus from the terminal apparatus, and determining whether a patient corresponding to the identification information of the smart card is assigned to a caregiver corresponding to the identification information of the terminal apparatus.

When the encrypted data further includes a hash value generated by the smart card, the method of the management server may further include determining whether the encrypted data is falsified based on a hash value generated by decrypting the encrypted data.

The method of the management server may further include: receiving, from the terminal apparatus, biometric information of a caregiver in possession of the terminal apparatus and identification information of the terminal apparatus; comparing the biometric information received from the terminal apparatus with biometric information of the caregiver corresponding to the identification information of the terminal apparatus; determining whether the caregiver in possession of the terminal apparatus matches with the caregiver corresponding to the identification information of the terminal apparatus; and if a match is not determined, storing, in the storage circuit, information indicating that the care service for the patient has not been normally performed.

When the time information is first time information that is generated when the smart card is first recognized by the terminal apparatus, and the encrypted data is first encrypted data including encrypted first time information, the method of the management server may further include: receiving second encrypted data including encrypted second time information from the terminal apparatus, the encrypted second time information being obtained by encrypting, by the smart card, the second time information corresponding to a point in time when the smart card is recognized a second time by the terminal apparatus; and decrypting the second encrypted data to acquire the second time information. The storage circuit may store a time related to the care service for the patient based on the second time information, and The management server may store a care service start time and a care service end time based on the first time information and the second time information, respectively.

When a care schedule request and identification information of the terminal apparatus are received from the terminal apparatus, the method of the management server may further include transmitting, to the terminal apparatus, care schedule data of patients assigned to the caregiver corresponding to the identification information of the terminal apparatus.

The method of the management server may further include transmitting a push message indicating a change of a care schedule, which corresponds to the care schedule data, to the terminal apparatus if the care schedule is changed after the care schedule data has been transmitted to the terminal apparatus.

A smart card of a patient includes: a memory having stored therein instructions; and a processor being controlled by the instructions and performing a method, the method including: recognizing a terminal apparatus of a caregiver; encrypting time information corresponding to a point in time when the smart card recognizes the terminal apparatus to generate encrypted time information; generating encrypted data including the encrypted time information; and transmitting the encrypted data to the terminal apparatus.

The method of the smart card may further include acquiring the time information.

The time information may be provided by the terminal apparatus.

A non-transitory computer readable medium has stored thereon a program that, when executed, causes a processor to perform a method, the method including: recognizing a smart card of a patient; receiving encrypted data including encrypted time information from the smart card, the encrypted time information being generated at the smart card by encrypting time information corresponding to a point in time when the terminal apparatus recognizes the smart card; and transmitting the encrypted data to a management server.

A non-transitory computer readable medium has stored thereon a program that, when executed, causes a processor to perform a method, the method including: receiving encrypted data including encrypted time information from a terminal apparatus of a caregiver, the encrypted time information being obtained by encrypting, at a smart card of a patient, time information corresponding to a point in time when the smart card is recognized by the terminal apparatus; decrypting the encrypted data to acquire the time information; and storing a time related to a care service for the patient based on the time information.

It is to be understood that both the foregoing general description and the following detailed description of embodiments are not limiting, but are intended to provide further explanation of the invention as claimed.

BRIEF DESCRIPTION OF THE DRAWINGS

FIG. 9 illustrates care schedule data output by a management server according to an embodiment of the present disclosure.

DESCRIPTION OF SPECIFIC EMBODIMENTS

Figure 1:
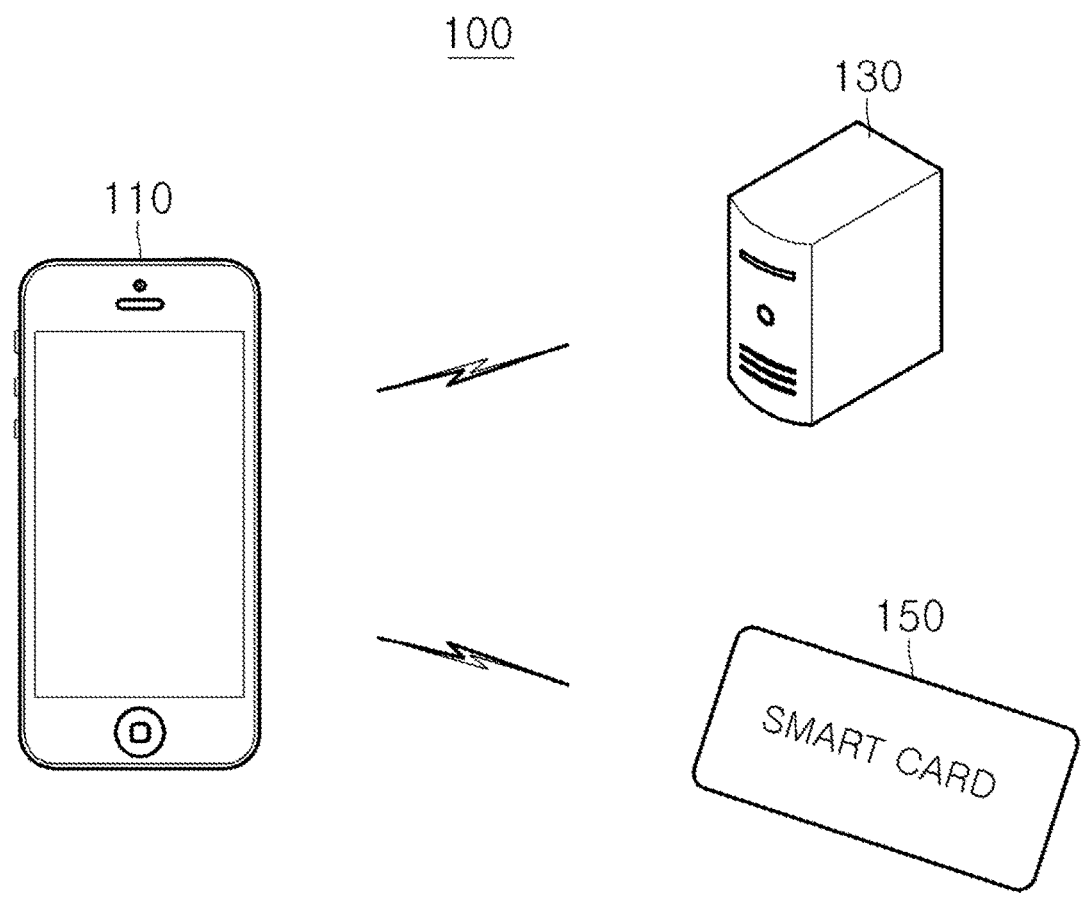
FIG. 1 illustrates a system for managing a care service according to an embodiment of the present disclosure.

Various embodiments will be described below in more detail with reference to the accompanying drawings. The present invention may, however, include embodiments in different forms and should not be construed as limited to the embodiments set forth herein. Rather, these embodiments are provided so that this disclosure will be thorough and complete, and will fully convey the scope of the present disclosure to those skilled in the art. Throughout the disclosure, like reference numerals refer to like parts in the various figures and embodiments of the present disclosure. The drawings are not necessarily to scale and in some instances, proportions may have been exaggerated in order to clearly illustrate features of the embodiments.

FIG. 1 illustrates a system 100 for managing a care service according to an embodiment of the present disclosure. The system 100 includes a terminal apparatus 110, a smart card 150, and a management server 130.

The terminal apparatus 110 is held by a caregiver, and the smart card 150 is held by a patient. The care service provided to the patient may be managed by establishing a local area network channel between the terminal apparatus 110 and the smart card 150 and transmitting/receiving relevant data over the local area network channel. In FIG. 1, the terminal apparatus 110 is illustrated as a smartphone. However, in another embodiment, the terminal apparatus 110 may be any mobile device such as a mobile phone, a personal digital assistant (PDA), a notebook, a tablet PC, and the like.

The management server 130 manages patient care schedule data, time information related to the car service for the patient, and the like. The management server 130 and the terminal apparatus 110 may transmit/receive relevant data through a wireless communication network such as Wi-Fi, 3G, LTE, or the like.

In the system 100, the terminal apparatus 110 and the smart card 150 transmit/receive time information related to the care service over the local area network channel. The terminal apparatus 110 transmits the time information to the management server 130 when the terminal apparatus 110 is connected to the management server 130 through the network. Therefore, the terminal apparatus 110 and the management server 130 can manage information related to providing a care service to a patient even if the network connection between the terminal apparatus 110 and the management server 130 is unstable.

Hereinafter, an operation of the terminal apparatus 110 according to an embodiment of the present disclosure will be described with reference to FIG. 2.

Figure 2:
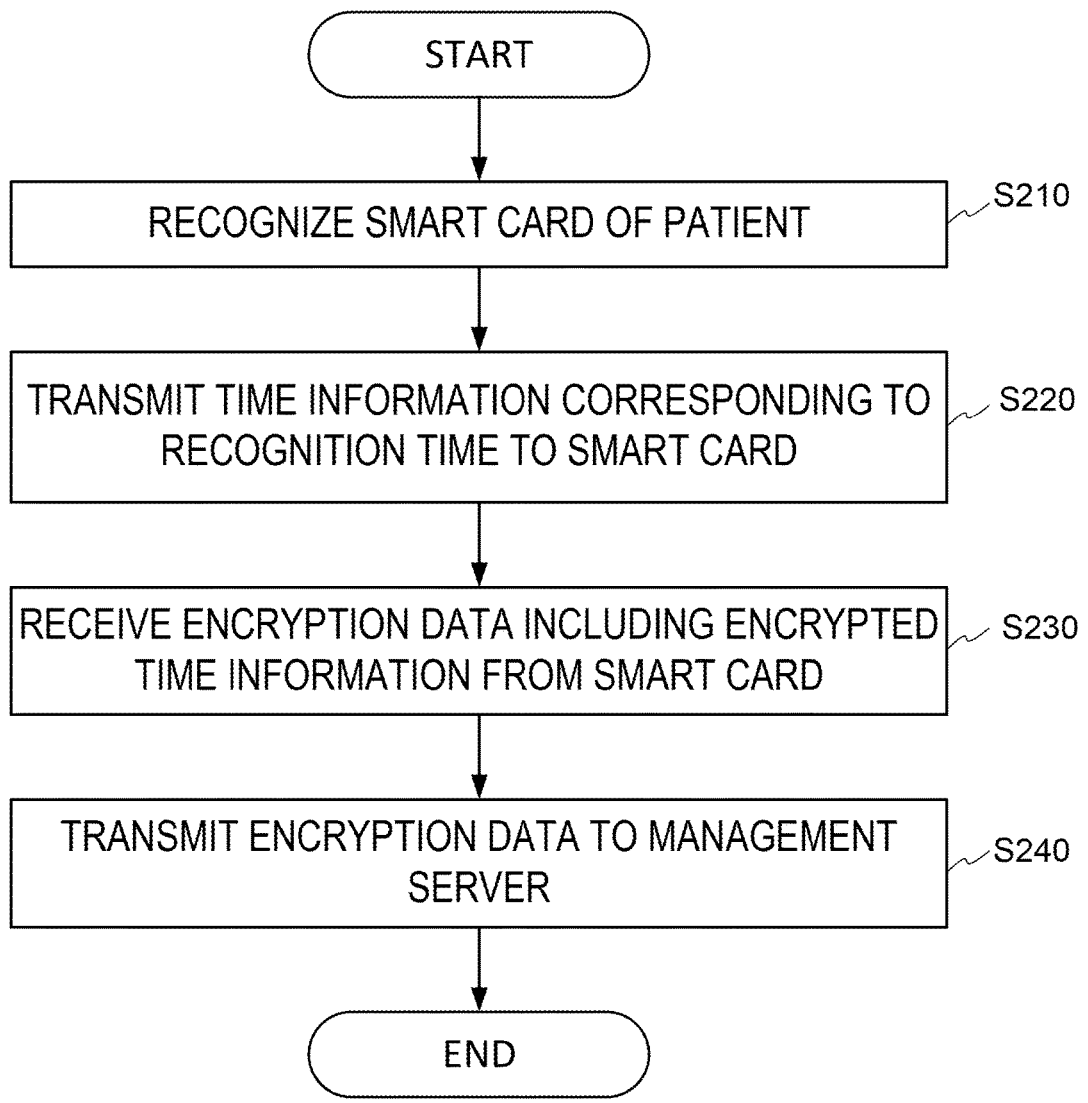
FIG. 2 is a flowchart illustrating a method for managing, by a terminal apparatus, a care service according to an embodiment of the present disclosure.

FIG. 2 is a flowchart illustrating a method for managing, by a terminal apparatus, a care service according to an embodiment of the present disclosure.

At step S210, the terminal apparatus 110 of a caregiver recognizes the smart card 150 of a patient. When the smart card 150 is recognized by the terminal apparatus 110, the terminal apparatus 110 establishes a local area network channel with the smart card 150. When the caregiver, who holds the terminal apparatus 110, visits a house or a sanatorium where the patient resides, the caregiver uses the terminal apparatus 110 to recognize the smart card 150 held by the patient. In an embodiment, the terminal apparatus 110 recognizes the smart card 150 after sliding the smart card 150 through a card recognizer or tapping the smart card 150 to a card recognizer. The card recognizer for recognizing the smart card 150 may be embedded in the terminal apparatus 110 or may be a dongle-type card recognizer that is capable of being connected to a connection port of the terminal apparatus 110.

At step S220, the terminal apparatus 110 transmits, to the smart card 150, time information corresponding to a point in time when the smart card 150 is recognized by the terminal apparatus 110. For example, if the smart card 150 is recognized at 1:00 p.m., the terminal apparatus 110 may transmit information indicating 1:00 p.m. or information corresponding to 1:00 p.m. to the smart card 150 as the time information.

At step S230, the terminal apparatus 110 receives encrypted data from the smart card 150. The encrypted data is generated by the smart card 150 using an encryption key pre-stored in the smart card 150. The encrypted data may include encrypted time information that is generated based on the time information. The encrypted data may further include encrypted identification information of the smart card 150. The encrypted data may still further include a hash value of the smart card 150. Since the terminal apparatus 110 stores no decryption key for decrypting the encrypted data transmitted from the smart card 150, the caregiver holding the terminal apparatus 110 cannot change the encrypted time information included in the encrypted data.

At step S240, the terminal apparatus 110 transmits the encrypted data to the management server 130. The management server 130 stores a decryption key capable of decrypting the encrypted data. Therefore, the management server 130 acquires the time information by decrypting the encrypted data received from the terminal apparatus 110, and stores a time related to the care service for the patient based on the time information.

Before transmitting the encrypted data to the management server 130, the terminal apparatus 110 may check whether the terminal apparatus 110 can connect to the management server 130 through a network. As a result of the checking, if it is determined that the terminal apparatus 110 can connect to the management server 130 through the network, the terminal apparatus 110 transmits the encrypted data to the management server 130. If it is determined that the terminal apparatus 110 cannot connect to the management server 130 through the network, the terminal apparatus 110 stores the encrypted data in a storage circuit therein, and after a predetermined time has elapsed, the terminal apparatus 110 may check again whether the terminal apparatus 110 can connect to the management server 130 through the network. Then, when it is determined that the terminal apparatus 110 can connect to the management server 130 through the network, the terminal apparatus 110 is connected to the management server 130 and transmits the encrypted data to the management server 130. The time related to the care service may include a care service start time and a care service end time.

If the encrypted data includes the encrypted identification information of the smart card 150, the management server 130 may determine which patient corresponds to identification information of the smart card 150 among a plurality of patients based on the identification information extracted from the encrypted data, and then store a time related to a care service for the determined patient based on the time information acquired from the encrypted data.

As described above, when the terminal apparatus 110 is not connected to the management server 130, the encrypted data including the encrypted time information is stored in the storage circuit of the terminal apparatus 110, and then, when connected to the management server 130, the terminal apparatus 110 transmits the stored encrypted data to the management server 130.

Therefore, the time information related to the care service can be protected from falsification, while being created and managed, even if the terminal apparatus 110 and the management server 130 are not connected through a network. The terminal apparatus 110 receives, from the smart card 150, the encrypted data generated by the smart card 150. Therefore, a user of the terminal apparatus 110, e.g., the caregiver holding the terminal apparatus 110, cannot falsify the time information included in the encrypted data. In other words, if the terminal apparatus 110 were to store unencrypted time information itself, there would be a risk that the time information could be falsified by the caregiver while the terminal apparatus 110 is not connected to the management server 130. Therefore, to prevent the caregiver from falsifying the time information, the time information is encrypted by the smart card 150 and then transmitted to the terminal apparatus 110, and the terminal apparatus 110 stores the encrypted data, including the encrypted time information.

Figure 3:
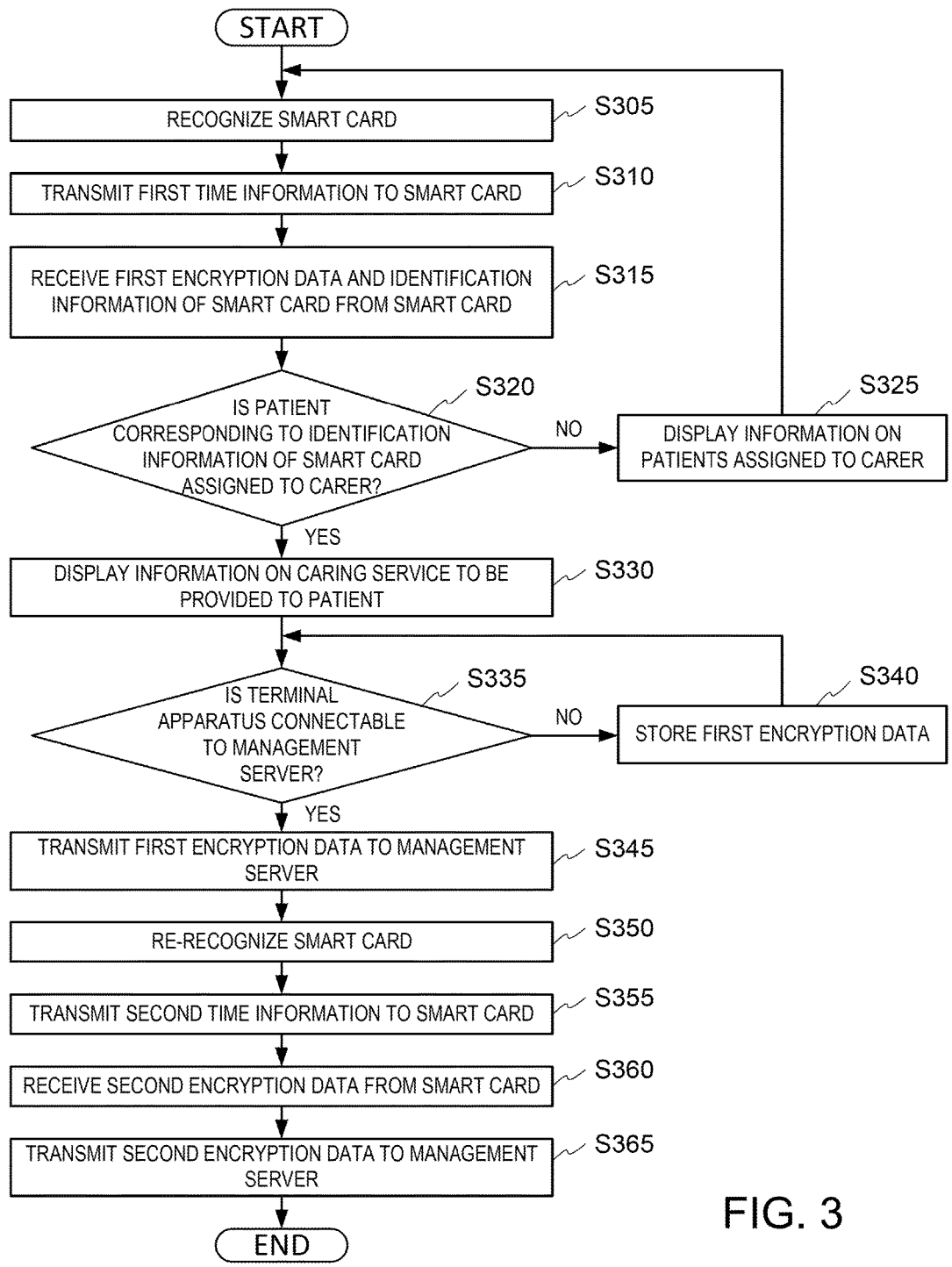
FIG. 3 is a flowchart illustrating details of a method for managing a care service of FIG. 2 according to an embodiment of the present disclosure.

FIG. 3 is a flowchart illustrating a method for managing, by the terminal apparatus 110, a care service according to an embodiment of the present disclosure. The flowchart of FIG. 3 provides more detailed processes of the method for managing the care service, which is illustrated in FIG. 2.

At step S305, the terminal apparatus 110 of a caregiver recognizes the smart card 150 of a patient.

At step S310, the terminal apparatus 110 transmits, to the smart card 150, first time information. The first time information corresponds to a point in time when the smart card 150 is first recognized by the terminal apparatus 110 when the caregiver visits the patient.

At step S315, the terminal apparatus 110 receives, from the smart card 150, first encrypted data. The first encrypted data includes encrypted first time information and encrypted identification information of the smart card 150. In addition to the first encrypted data including the encrypted first time information and the encrypted identification information of the smart card 150, the terminal apparatus 110 may receive unencrypted identification information of the smart card 150. The encrypted identification information of the smart card 150, which is included in the first encrypted data, is information to be used by the management server 130, and the unencrypted identification information of the smart card 150 is information to be used by the terminal apparatus 110.

At step S320, the terminal apparatus 110 determines whether the patient corresponding to the identification information of the smart card 150 is assigned to the caregiver using the unencrypted identification information from the smart card 150. The terminal apparatus 110 has pre-stored information on patients assigned to the caregiver. The pre-stored information may include identification information of smart cards held by the patients assigned to the caregiver. Therefore, if the unencrypted identification information of the smart card 150 is provided, the terminal apparatus 110 compares the pre-stored information with the unencrypted identification information of the smart card 150 and determines whether the patient whom the caregiver visits, i.e., the patient holding the smart card 150, is a patient assigned to the caregiver.

If it is determined that the patient whom the caregiver visits is not a patient assigned to the caregiver, this means that the visit of the caregiver is made in error. Therefore, at step S325, the terminal apparatus 110 outputs information on the patients assigned to the caregiver, e.g., information on patients whom the caregiver is responsible for visiting.

On the other hand, if it is determined that the patient whom the caregiver visits is a patient assigned to the caregiver, at step S330, the terminal apparatus 110 outputs information on a care service to be provided to the patient whom the caregiver visits.

At step S335, the terminal apparatus 110 determines whether the terminal apparatus 110 can connect to the management server 130 through the network.

If it is determined that the terminal apparatus 110 cannot connect to the management server 130 through the network, at step S340, the terminal apparatus 110 stores the first encrypted data in a storage circuit therein.

If it is determined that the terminal apparatus 110 can connect to the management server 130 through the network, at step S345, the terminal apparatus 110 is connected to the management server 130 through the network and transmits the first encrypted data to the management server 130. As described above with reference to FIG. 2, since the terminal apparatus 110 does not have a decryption key capable of decrypting the first encrypted data, the caregiver cannot falsify the encrypted first time information included in the first encrypted data. The management server 130 may acquire the first time information by decrypting the first encrypted data using a decryption key, and store a care service start time for the patient holding the smart card 150 based on the first time information. The management server 130 may store a first time corresponding to the first time information as the care service start time, or may store a time having a predetermined time difference from the first time as the care service start time.

At step S350, the terminal apparatus 110 re-recognizes the smart card 150 of the patient.

At step S355, the terminal apparatus 110 transmits, to the smart card 150, second time information. The second time information corresponds to a point in time when the smart card 150 of the patient is re-recognized by the terminal apparatus 110.

At step S360, the terminal apparatus 110 receives second encrypted data. The second encrypted data includes encrypted second time information from the smart card 150 of the patient. The second encrypted data is generated by the smart card 150 using the encryption key pre-stored in the smart card 150. In addition to the encrypted second time information, the second encrypted data may further include the encrypted identification information of the smart card 150. Furthermore, the smart card 150 may transmit the unencrypted identification information of the smart card 150 to the terminal apparatus 110 together with the second encrypted data. As at step S320, the terminal apparatus 110 may use the unencrypted identification information of the smart card 150 to determine whether the patient corresponding to the identification information of the smart card 150 is assigned to the caregiver.

At step S365, the terminal apparatus 110 transmits the second encrypted data to the management server 130. As described above, when the terminal apparatus 110 can connect to the management server 130 through the network, the terminal apparatus 110 is connected to the management server 130 and transmits the second encrypted data to the management server 130. When the terminal apparatus 110 cannot connect to the management server 130 through the network, the terminal apparatus 110 stores the second encrypted data in the storage circuit therein.

The management server 130 may acquire the second time information by decrypting the second encrypted data using the decryption key, and store a care service end time for the patient based on the second time information. The management server 130 may store a second time corresponding to the second time information as the care service end time, or may store a time having a predetermined time difference from the second time as the care service end time.

When the same identification information of the smart card 150 is included in the first encrypted data and the second encrypted data, the management server 130 may determine a patient corresponding to the identification information of the smart card 150, and store the care service start time for the determined patient based on the first time information acquired from the first encrypted data. Then, when the management server 130 receives the second encrypted data including the same identification information as the identification information of the smart card 150 which is included in the first encrypted data, the management server 130 may store the care service end time for the determined patient based on the second time information acquired from the second encrypted data.

On the other hand, if the identification information included in the second encrypted data is different from the identification information included in the first encrypted data, the management server 130 may store a time corresponding to the second time information included in the second encrypted data as a care service start time for another patient corresponding to the identification information included in the second encrypted data.

Meanwhile, in an embodiment, the terminal apparatus 110 may receive condition information of a patient that the caregiver inputs. The condition information of the patient may include information on the patient's conditions and is obtained while the caregiver provides the care service to the patient. The terminal apparatus 110 may transmit the condition information of the patient to the management server 130.

In addition, the terminal apparatus 110 may receive biometric information from the caregiver, and use the biometric information to authenticate whether the caregiver holding the terminal apparatus 110 is an authorized caregiver. In order to prevent a third party, i.e., an unauthorized caregiver, from providing care and using the terminal apparatus 110 of an authorized caregiver, the terminal apparatus 110 receives biometric information, such as a fingerprint, iris information, or voice, from a caregiver holding the terminal apparatus 110, and compares the received biometric information with pre-stored biometric information of the authorized caregiver to authenticate the caregiver holding the terminal apparatus 110.

Furthermore, the terminal apparatus 110 may prevent the caregiver from modifying a present time determined by the terminal apparatus 110. The terminal apparatus 110 may acquire the first time information corresponding to a point in time when the smart card 150 is recognized by the terminal apparatus 110, while determining the present time. This is because the accuracy of the first time information cannot be ensured if the present time itself determined by the terminal apparatus 110 is falsified by the caregiver.

The terminal apparatus 110 may receive care schedule data from the management server 130, which will be described with reference to FIGS. 4 and 5.

Figure 4:
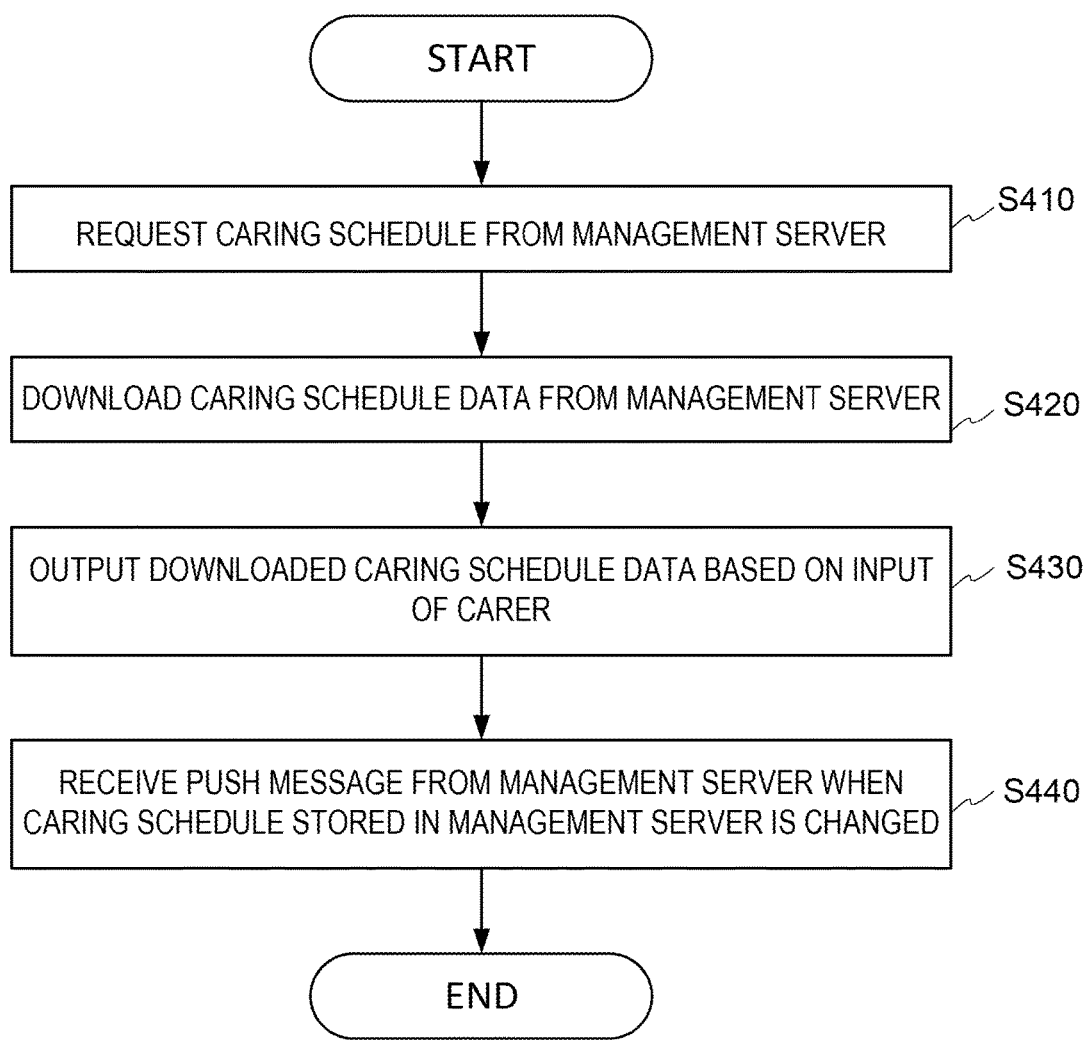
FIG. 4 is a flowchart illustrating a method for receiving, by a terminal apparatus, care schedule data from a management server according to an embodiment of the present disclosure.
Figure 5:
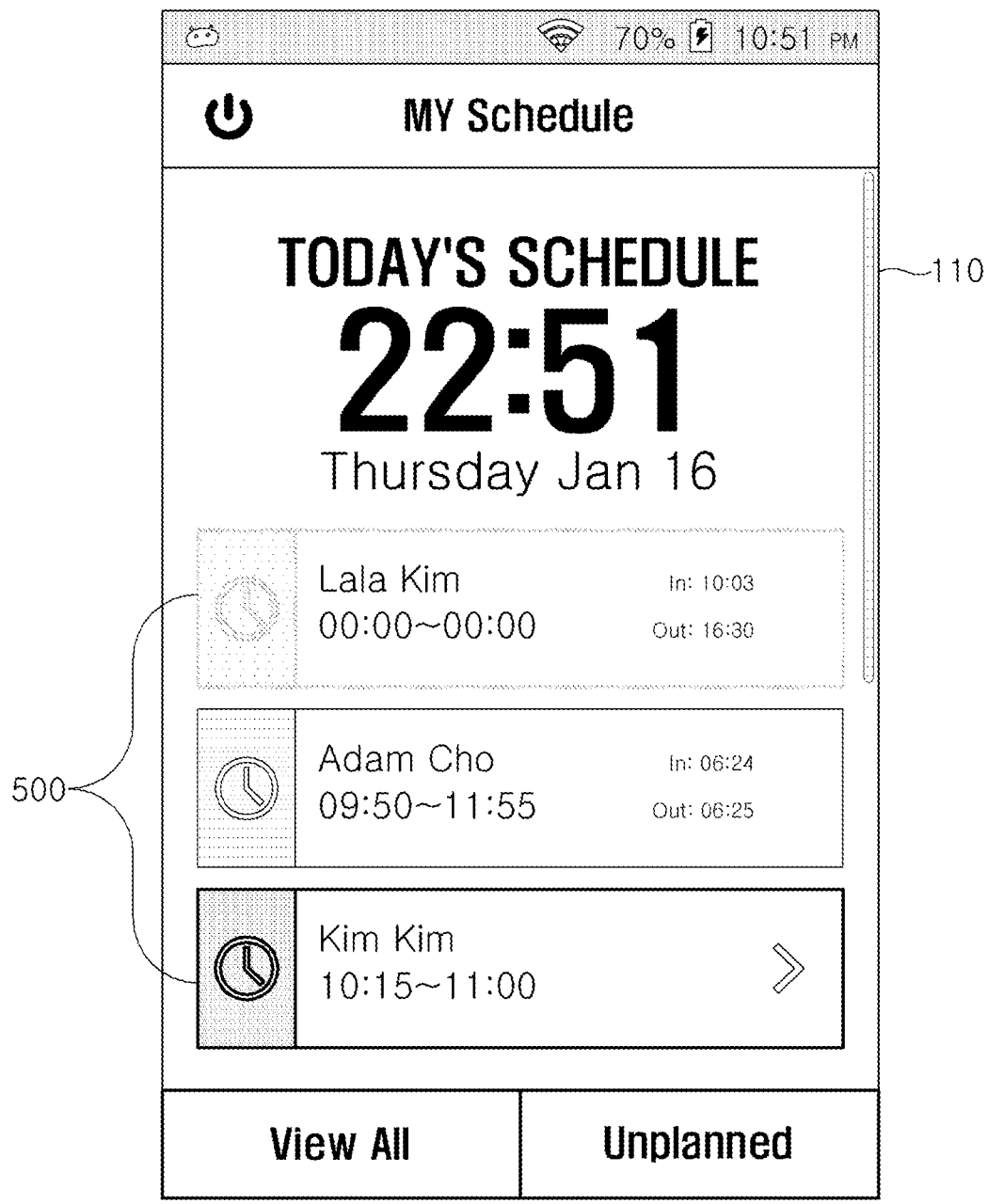
FIG. 5 illustrates care schedule data output by a terminal apparatus according to an embodiment of the present disclosure.

FIG. 4 is a flowchart illustrating a method for receiving, by the terminal apparatus 110, care schedule data from the management server 130 according to an embodiment of the present disclosure, and FIG. 5 illustrates care schedule data 500 output by the terminal apparatus 110 according to an embodiment of the present disclosure.

At step S410, the terminal apparatus 110 requests a care schedule from the management server 130. While requesting the care schedule from the management server 130, the terminal apparatus 110 may also transmit its own identification information to the management server 130.

At step S420, the terminal apparatus 110 downloads care schedule data from the management server 130. When there is care schedule data corresponding to identification information of a plurality of terminal apparatuses, the management server 130 may select care schedule data corresponding to the identification information of the terminal apparatus 110 and transmit the selected care schedule data to the terminal apparatus 110.

At step S430, the terminal apparatus 110 outputs the downloaded care schedule data based on the input of the caregiver. FIG. 5 illustrates care schedule data 500 output in a webpage form by the terminal apparatus 110. The care schedule data 500 in the webpage form is output when the terminal apparatus 110 is connected to the management server 130 through the network. The caregiver may confirm a patient and a time that the caregiver is supposed to visit the patient with reference to the care schedule data 500 output from the terminal apparatus 110.

In another embodiment, instead of receiving the care schedule data from the management server 130 in the webpage form as shown in FIG. 5, the terminal apparatus 110 downloads the care schedule data in a file form. Therefore, the terminal apparatus 110 can output the downloaded care schedule data even when the terminal apparatus 110 is not connected to the management server 130 through the network.

At step S440, if the care schedule stored in the management server 130 is changed after having been transmitted to the terminal apparatus 110, the terminal apparatus 110 receives a push message from the management server 130. When the terminal apparatus 110 receives the push message, the caregiver may recognize that the care schedule is changed, and may confirm the changed care schedule by downloading changed care schedule data from the management server 130.

Meanwhile, in an embodiment, if the smart card 150 of the patient is not recognized by the terminal apparatus 110 of the caregiver within a predetermined time interval from a visit reservation time for the patient assigned to the caregiver, the terminal apparatus 110 may output an alarm message to notify the caregiver of information on the patient to be visited, with reference to the care schedule data 500 received from the management server 130.

Figure 6:
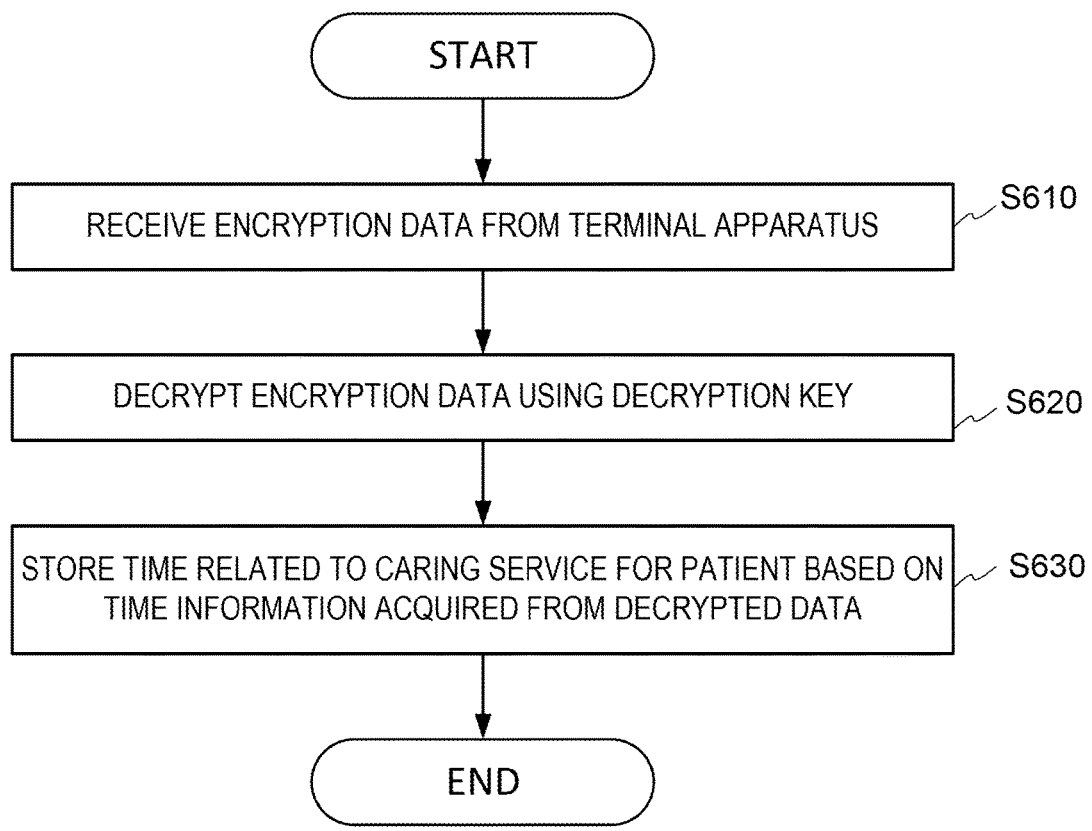
FIG. 6 is a flowchart illustrating a method for managing, by a management server, a care service according to an embodiment of the present disclosure.

Hereinafter, an operation of a management server according to an embodiment of the present disclosure will be described with reference to FIG. 6. FIG. 6 is a flowchart illustrating a method for managing, by the management server, a care service according to an embodiment of the present disclosure.

At step S610, the management server 130 receives, from the terminal apparatus 110, encrypted data, including encrypted time information corresponding to a point in time when the smart card 150 of a patient is recognized by the terminal apparatus 110 of a caregiver. As described above, the encrypted data is generated by the smart card 150 using an encryption key and is transmitted to the terminal apparatus 110. The encrypted data may further include encrypted identification information of the smart card 150.

At step S620, the management server 130 decrypts the encrypted data using a decryption key corresponding to the encryption key stored in the smart card 150.

At step S630, the management server 130 stores a time related to a care service for the patient based on the time information acquired by decrypting the encrypted data. That is, when the identification information of the smart card 150 is included in the encrypted data, the management server 130 may determine which patient corresponds to the identification information of the smart card 150 and store the time related to the care service for the determined patient based on the time information. The time information may include any one or both of first time information corresponding to a care service start time and second time information corresponding to a care service end time.

Figure 7:
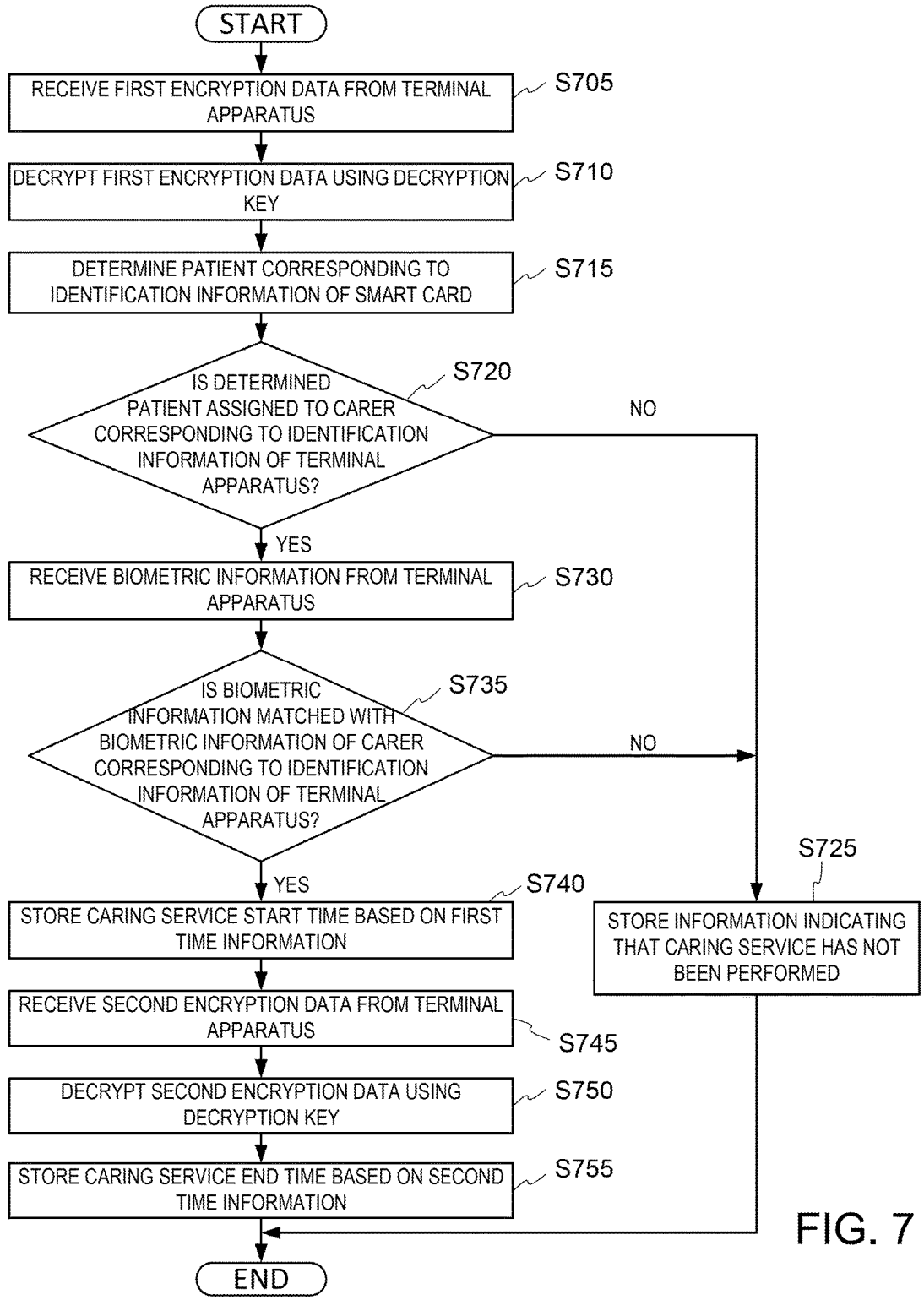
FIG. 7 is a flowchart illustrating details of a method for managing a care service of FIG. 6 according to an embodiment of the present disclosure.

FIG. 7 is a flowchart illustrating a method for managing, by a management server, a care service according to an embodiment of the present disclosure. The flowchart of FIG. 7 illustrates more detailed processes of a method for managing a care service in accordance with an embodiment.

At step S705, the management server 130 receives first encrypted data. The first encrypted data includes encrypted first time information, which corresponds to a point in time when the smart card 150 of a patient is recognized by the terminal apparatus 110 of a caregiver, and encrypted identification information of the smart card 150.

At step S710, the management server 130 acquires first time information and identification information of the smart card 150 by decrypting the first encrypted data using a decryption key.

At step S715, the management server 130 determines which patient corresponds to the identification information of the smart card 150 from among a plurality of patients.

At step S720, the management server 130 determines whether the determined patient is assigned to the caregiver corresponding to the identification information of the terminal apparatus 110. While receiving the first encrypted data from the terminal apparatus 110, the management server 130 may also receive the identification information of the terminal apparatus 110.

If it is determined that the patient corresponding to the smart card 150 is not assigned to the caregiver corresponding to the identification information of the terminal apparatus 110, at step S725, the management server 130 stores, in a storage circuit therein, information indicating that the care service for the patient has not been performed. Since the patient is not assigned to the caregiver corresponding to the identification information of the terminal apparatus 110, another caregiver, who has no responsibility for the patient, has visited the patient.

On the other hand, if it is determined that the patient is assigned to the caregiver corresponding to the identification information of the terminal apparatus 110, at step S730, the management server 130 further receives biometric information of a caregiver holding the terminal apparatus 110 from the terminal apparatus 110.

At step S735, the management server 130 determines whether the received biometric information matches with biometric information of the caregiver corresponding to the identification information of the terminal apparatus 110. The management server 130 may have pre-stored biometric information of a plurality of caregivers. The biometric information of each of the plurality of caregivers may be stored as a match with identification information of each of a plurality of terminal apparatuses used by the plurality of caregivers.

When the biometric information received from the terminal apparatus 110 does not match with the biometric information that is pre-stored in the management server 130 and corresponds to the identification information of the terminal apparatus 110, at step S725, the management server 130 stores, in the storage circuit, information indicating that the care service for the patient has not been performed. This is because a third party, i.e., an unauthorized caregiver, has visited the patient while holding the terminal apparatus 110. In an embodiment, the management server 130 also stores information indicating that an unauthorized caregiver has visited the patient. In an embodiment, the management server 130 transmits this information to a service provider or other authority.

When the biometric information received from the terminal apparatus 110 matches with the biometric information that is pre-stored in the management server 130 and corresponds to the identification information of the terminal apparatus 110, at step S740, the management server 130 stores a care service start time for the patient based on a first time corresponding to the first time information.

The management server 130 may store the first time itself as the care service start time, or may store a time having a predetermined time difference from the first time as the care service start time.

At step S745, the management server 130 receives second encrypted data from the terminal apparatus 110. The second encrypted data includes encrypted second time information, which corresponds to a point in time when the smart card 150 of the patient is re-recognized by the terminal apparatus 110, and the encrypted identification information of the smart card 150.

At step S750, the management server 130 acquires second time information and the identification information of the smart card 150 by decrypting the second encrypted data using the decryption key. As in the case of step S720, the management server 130 may determine which patient corresponds to the identification information of the smart card 150, and determine whether the determined patient is assigned to the caregiver.

At step S755, the management server 130 stores a care service end time for the determined patient based on the second time information.

In an embodiment, the management server 130 stores the care service end time for the patient based on the second time information only when the identification information of the smart card 150, which is included in the second encrypted data, is identical to the identification information of the smart card 150 which is included in the first encrypted data.

FIG. 7 illustrates that the management server 130 receives the first encrypted data prior to the biometric information of the caregiver. However, according to another embodiment, the management server 130 may simultaneously receive the first encrypted data and the biometric information from the terminal apparatus 110. According to still another embodiment, the management server 130 may receive the biometric information prior to the first encrypted data and authorize the caregiver holding the terminal apparatus 110 before receiving the first encrypted data.

In an embodiment, a hash value generated by the smart card 150 may be included in the first encrypted data transmitted to the management server 130, and the management server 130 may confirm whether the first encrypted data has been falsified based on the hash value acquired by decrypting the first encrypted data. That is, if the caregiver falsifies information included in the first encrypted data, the hash value is also changed. Hence, the management server 130 may confirm whether the first encrypted data has been forged or falsified through a comparison of hash values.

The management server 130 may provide care schedule data to the terminal apparatus 110. A method of providing care schedule data in accordance with an embodiment will be described with reference to FIGS. 8 and 9.

Figure 8:
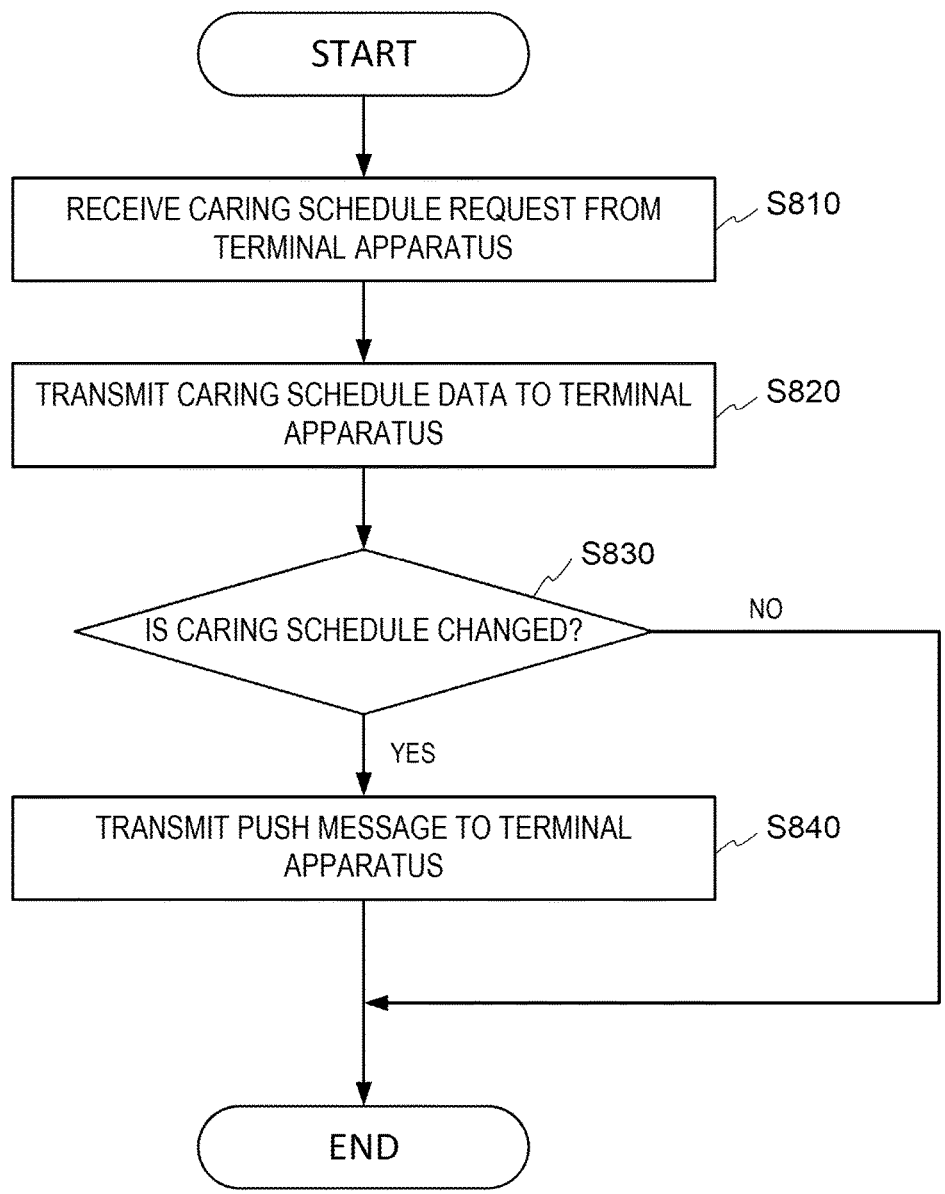
FIG. 8 is a flowchart illustrating a method for providing, by a management server, care schedule data to a terminal apparatus according to an embodiment of the present disclosure.

FIG. 8 is a flowchart illustrating a method for providing, by a management server, care schedule data to a terminal apparatus according to an embodiment of the present disclosure. FIG. 9 illustrates care schedule data output by a management server according to an embodiment of the present disclosure.

At step S810, the management server 130 receives a request for a care schedule, i.e., a care schedule request, from the terminal apparatus 110. In addition to the care schedule request, the management server 130 may receive identification information of the terminal apparatus 110.

The management server 130 may store information on each of a plurality of patients and a care schedule for each of the plurality of patients. The information on each of the plurality of patients may include a name, an address, and/or an identification number of a smart card of each of the plurality of patients. The care schedule for each of the plurality of patients may include a scheduled start time and a scheduled end time of a care service to be provided to each of the plurality of patients. The information on each of the plurality of patients and the care schedule for each of the plurality of patients may be stored as a match with a corresponding caregiver and/or identification information of a terminal apparatus of the corresponding caregiver. The information on each of the plurality of patients and the care schedule for each of the plurality of patients may be modified by an administrator.

As illustrated in FIG. 9, the management server 130 outputs a care schedule 910 for each of the plurality of patients, a name 920 of each of the plurality of patients, and a name 930 of a caregiver assigned to each of the plurality of patients. In addition, when a home-care service is provided by a caregiver, the management server 130 also outputs a care service start time 940 and a care service end time 950 of a corresponding caregiver.

At step S820, the management server 130 transmits, to the terminal apparatus 110, care schedule data for a patient assigned to a caregiver corresponding to the identification information of the terminal apparatus 110. The management server 130 may provide the care schedule data in a file form or a webpage form. As a result, the terminal apparatus 110 can check the care schedule data in the file form even when the terminal apparatus 110 is not connected to the management server 130 through a network.

At step S830, the management server 130 determines whether the care schedule has changed after having been initially transmitted to the terminal apparatus 110.

If it is determined that the care schedule has changed, at step S840, the management server 130 transmits, to the terminal apparatus 110, a push message indicating that the care schedule is changed. The terminal apparatus 110 downloads changed care schedule data.

Figure 10:
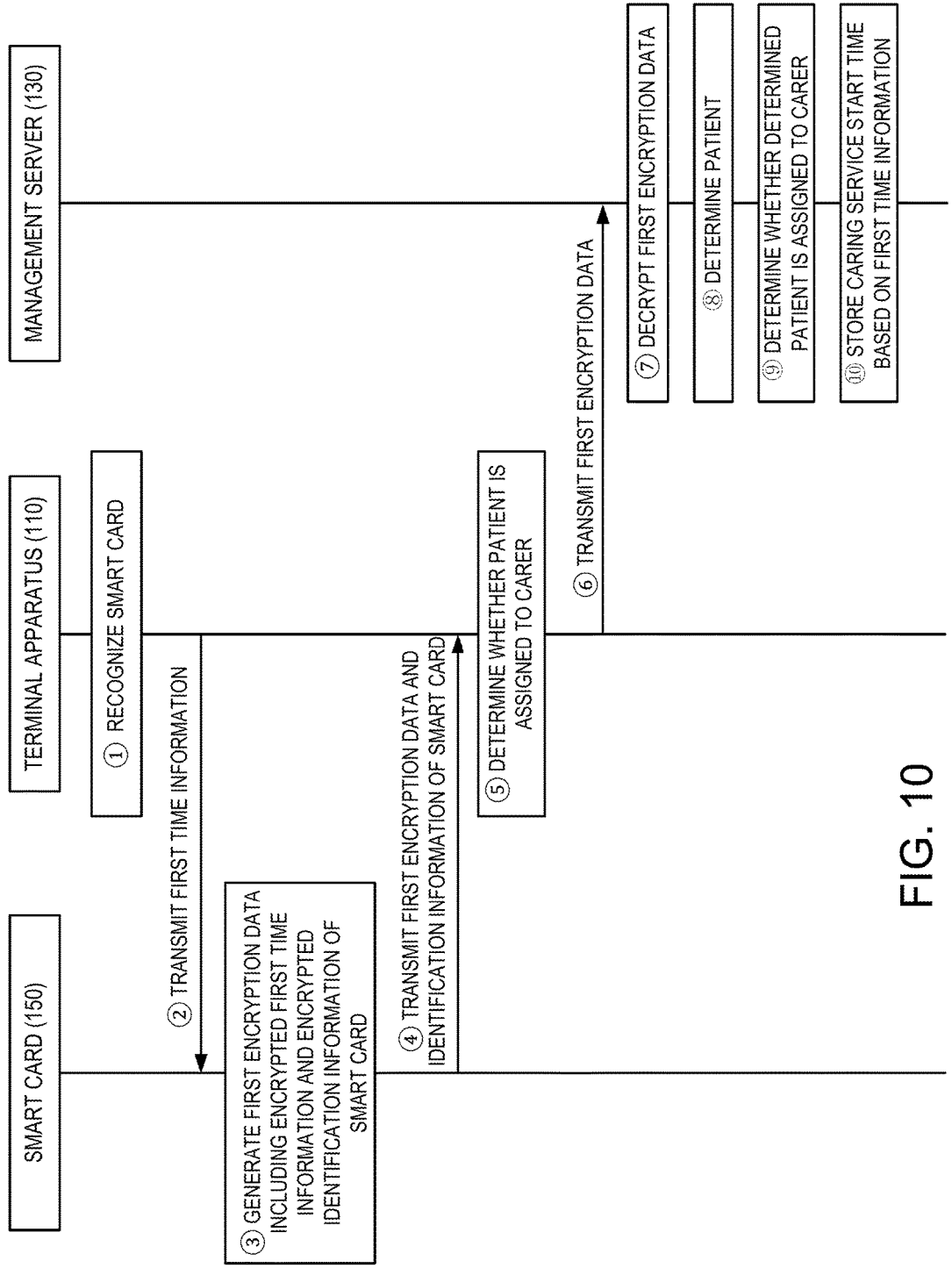
FIG. 10 is a flow diagram illustrating an operation of a system for managing a care service according to an embodiment of the present disclosure.

FIG. 10 illustrates an operation of a system for managing a care service according to an embodiment of the present disclosure.

① The terminal apparatus 110 recognizes the smart card 150 of a patient. ② The terminal apparatus 110 transmits, to the smart card 150, first time information corresponding to a point in time when the smart card 150 is recognized by the terminal apparatus 110. ③ The smart card 150 generates first encrypted data, including encrypted first time information and encrypted identification information of the smart card 150, by encrypting the first time information and identification information of the smart card 150 using a pre-stored encryption key. In another embodiment, the identification information of the smart card 150 may not be included in the first encrypted data.

④ The smart card 150 transmits the first encrypted data and unencrypted identification information of the smart card 150 to the terminal apparatus 110. ⑤ The terminal apparatus 110 determines whether the patient corresponding to the smart card 150 is assigned to a caregiver corresponding to the terminal apparatus 110 using the unencrypted identification information of the smart card 150. The terminal apparatus 110 may determine whether the patient and the caregiver are matched with each other using the unencrypted identification information of the smart card 150.

When the patient and the caregiver are matched with each other, ⑥ the terminal apparatus 110 transmits the first encrypted data to the management server 130. ⑦ The management server 130 acquires the first time information and the identification information of the smart card 150 by decrypting the first encrypted data using a decryption key. ⑧ The management server 130 determines which patient corresponds to the identification information of the smart card 150 from among a plurality of patients whose information is stored in a storage circuit of the management server 130, and ⑨ the management server 130 determines whether the determined patient is assigned to the caregiver. Since whether the patient and the caregiver are matched with each other is determined again by the management server 130 and the identification information of the smart card 150, which is included in the first encrypted data, cannot be falsified by the terminal apparatus 110, the management server 130 can accurately determine whether the determined patient is assigned to the caregiver.

⑩ When the caregiver and the patient are matched with each other, the management server 130 stores a care service start time for the patient based on the first time information. Although not shown in FIG. 10, after the care service start time is stored in the management server 130, if second encrypted data, including encrypted second time information is received from the terminal apparatus 110, the management server 130 may store a care service end time for the patient based on second time information acquired from the second encrypted data.

Figure 11:
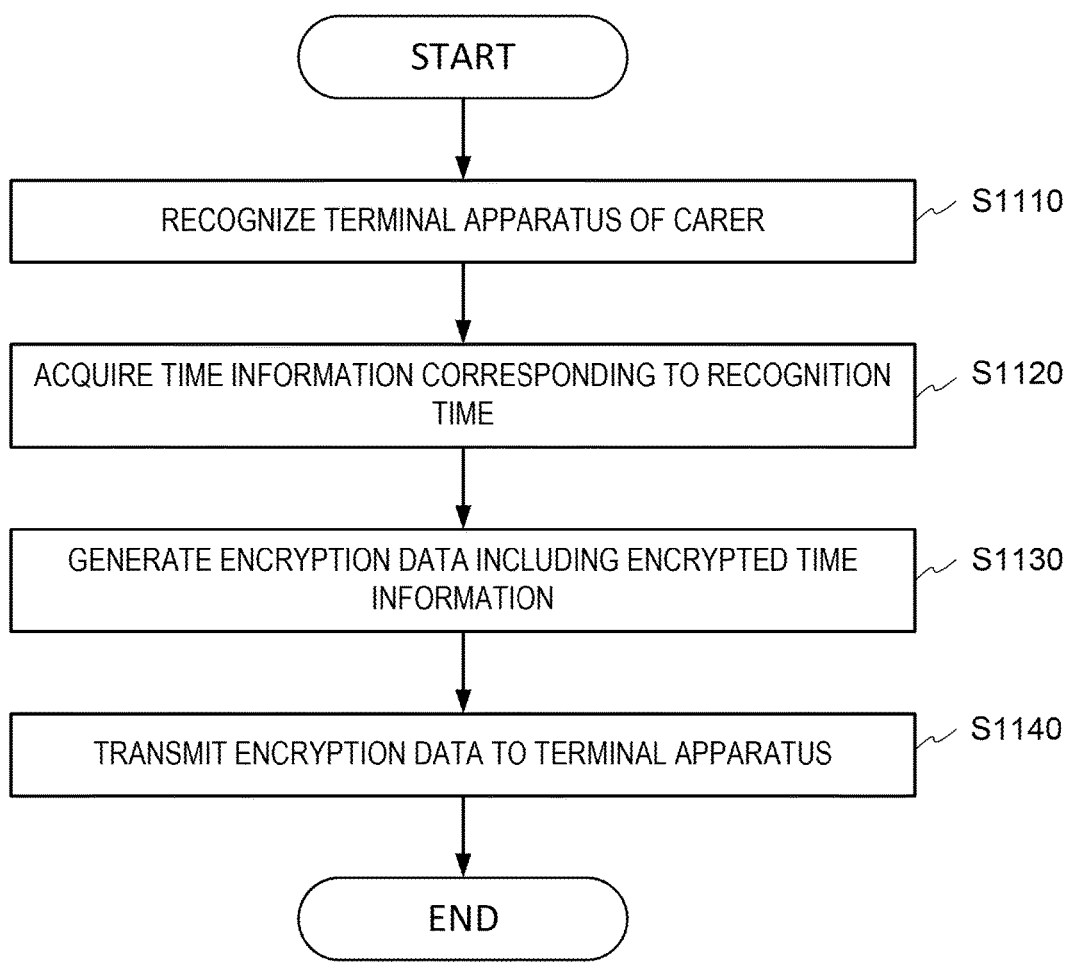
FIG. 11 is a flowchart illustrating a method for managing, by a smart card, a care service according to an embodiment of the present disclosure.

FIG. 11 is a flowchart illustrating a method for managing, by a smart card, a care service according to an embodiment of the present disclosure. In the above-described embodiments, the first time information and/or the second time information is acquired by the terminal apparatus 110 and is transmitted to the smart card 150. On the other hand, in the embodiment of FIG. 11, the first time information and/or the second time information is acquired by the smart card 150. As a result, it is possible to prevent the first time information and/or the second time information from being falsified by a caregiver.

At step S1110, the smart card 150 recognizes the terminal apparatus 110 of the caregiver. The smart card 150 may recognize the terminal apparatus 110 of the caregiver after tapping the smart card 150 to the card recognizer or sliding the smart card 150 through the card recognizer provided in the terminal apparatus 110.

At step S1120, the smart card 150 acquires time information corresponding to a point in time when the terminal apparatus 110 of the caregiver is recognized by the smart card 150. The smart card 150 may include a timer that determines a present time. The smart card 150 may acquire, as the time information, a time corresponding to a point in time when the terminal apparatus 110 of the caregiver is recognized in the process of determining the present time.

At step S1130, the smart card 150 generates encrypted data, including encrypted time information, using an encryption key. The smart card 150 may include encrypted identification information and a hash value in the encrypted data, in addition to the encrypted time information.

At step S1140, the smart card 150 transmits the encrypted data to the terminal apparatus 110. The encrypted data transmitted to the terminal apparatus 110 may be transmitted to the management server 130 and decrypted by the management server 130. The management server 130 may store a time related to a care service for the patient based on the time information acquired by decrypting the encrypted data. The time information may include any one or both of first time information corresponding to a care service start time and second time information corresponding to a care service end time.

Figure 12:
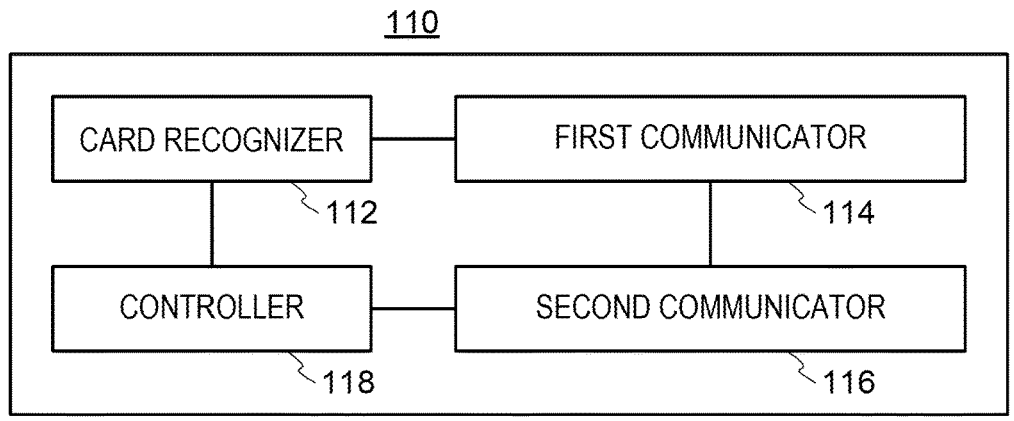
FIG. 12 illustrates a terminal apparatus according to an embodiment of the present disclosure.

FIG. 12 illustrates a terminal apparatus according to an embodiment of the present disclosure. The terminal apparatus 110 includes a card recognizer 112, a first communicator 114, a second communicator 116, and a controller 118, but embodiments are not limited thereto.

The card recognizer 112 may be embedded in the terminal apparatus 110, or may be connected to a connection port such as a USB port or an audio port of the terminal apparatus 110. The card recognizer 112 recognizes the smart card 150 of a patient whom a caregiver holding the terminal apparatus 110 visits. The smart card 150 may be recognized by the card recognizer 112 after tapping the smart card to the card recognizer 112 or sliding the smart card 150 through the card recognizer.

The first communicator 114 communicates with the smart card 150 through a local area network to transmit/receive data. The first communicator 114 transmits, to the smart card 150, time information corresponding to a point in time when the smart card 150 is recognized by the card recognizer 112, and receives, from the smart card 150, encrypted data, including encrypted time information and encrypted identification information of the smart card 150, which is generated through encryption by the smart card 150. The first communicator 114 may further receive unencrypted identification information of the smart card 150 from the smart card 150, in addition to the first encrypted data.

The second communicator 116 communicates with the management server 130 through a wireless communication network to transmit/receive data. When the second communicator 116 is connected to the management server 130 through a network, the second communicator 116 transmits the encrypted data to the management server 130. The management server 130 may acquire the time information by decrypting the encrypted data, and store a time related to a care service for the patient based on the time information.

The controller 118 controls respective components included in the terminal apparatus 110. The controller 118 may acquire time information corresponding to a point in time when the smart card 150 is recognized by the card recognizer 112 using present time information measured by a timer (not shown). The controller 118 may prevent the caregiver from modifying the present time information determined by the timer, and thus it is possible to prevent the falsification of the time information corresponding to the recognition time of the smart card 150. The controller 118 may determine whether the patient and the caregiver are matched with each other, whether the caregiver holding the terminal apparatus 110 is an authorized caregiver, and the like. Since such operations have been described above, detailed descriptions thereof are omitted. In an embodiment, the controller 118 includes a processor, a microprocessor, a central processing unit (CPU), or the like.

Although not illustrated in FIG. 12, the terminal apparatus 110 may further include a user input unit and an output unit.

The user input unit receives the input of the caregiver. The user input unit may include one or more of various input devices capable of receiving the input of the caregiver, for example, a keyboard, a mouse, a touchscreen, a voice recognizer, a biometric information recognizer, and the like. The caregiver can input condition information, which includes information about the condition of the patient, biometric information, and the like through the user input unit.

The output unit outputs information to the caregiver. The output unit may include one or more of various output devices including a display, a speaker, and the like. Specifically, the output unit may output information on a care service to be provided to the patient, an alarm message, care schedule data downloaded from the management server 130, and so on.

Figure 13:
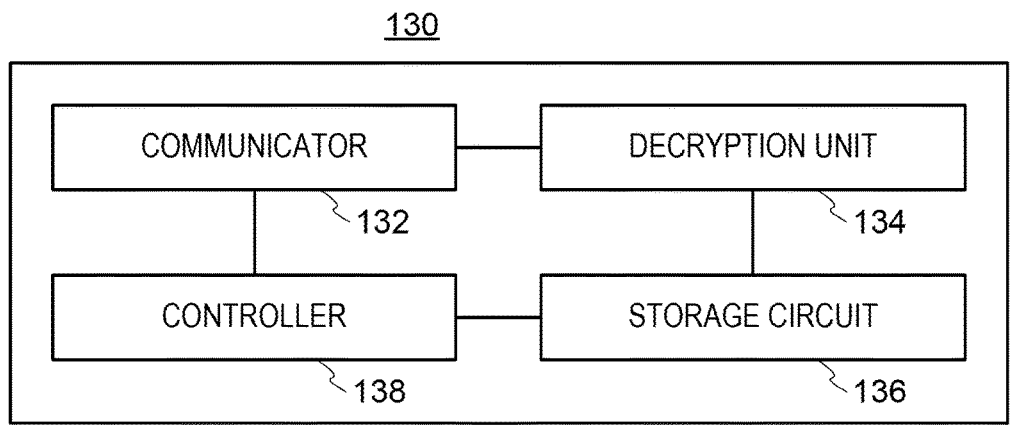
FIG. 13 illustrates a management server according to an embodiment of the present disclosure.

FIG. 13 illustrates a management server according to an embodiment of the present disclosure. The management server 130 includes a communicator 132, a decryption unit 134, a storage circuit 136, and a controller 138, but embodiments are not limited thereto.

The communicator 132 communicates with the terminal apparatus 110 through a wireless communication network to transmit/receive data. Specifically, the communicator 132 may receive encrypted data, biometric information, identification information, and the like from the terminal apparatus 110, and transmit care schedule data to the terminal apparatus 110 in response to a request from the terminal apparatus 110. In addition, if the care schedule data is changed after having been transmitted to the terminal apparatus 110, the communicator 132 may transmit, to the terminal apparatus 110, a push message indicating that the care schedule is changed.

The decryption unit 134 decrypts the encrypted data received from the terminal apparatus 110 using a decryption key pre-stored in the storage circuit 136.

The storage circuit 136 stores a time related to a care service for a patient based on time information acquired by decrypting the encrypted data. The storage circuit 136 may store information on a plurality of patients and a care schedule for each of the plurality of patients. The storage circuit 136 may store a care service start time and a care service end time for a corresponding patient based on the time information acquired from the encrypted data. In addition, the storage circuit 136 may store more information associated with the care service, such as information on caregivers including biometric information, identification information of terminal apparatuses, and the like.

The controller 138 controls respective components included in the management server 130. When identification information of the smart card 150 is acquired from the encrypted data, the controller 138 may determine which patient corresponds to the identification information of the smart card 150 from among the plurality of patients, and determine whether the patient is assigned to a caregiver corresponding to identification information of the terminal apparatus 110. In addition, the controller 138 may use the biometric information transmitted from the terminal apparatus 110 to determine whether the caregiver holding the terminal apparatus 110 is an authorized caregiver, and may use a hash value acquired from the encrypted data to determine whether the encrypted data has been forged or falsified. The biometric information includes biometric data of the caregiver of the terminal apparatus 110.

Operations performed by the controller 138 have been described for illustrative convenience, but embodiments are not limited thereto. The controller 138 may control other operations performed by the management server 130 that are described above with reference to other figures than FIG. 13.

In an embodiment, the controller 138 includes a processor, a microprocessor, a CPU, or the like.

Although not illustrated in FIG. 13, the management server 130 may further include a user input unit and an output unit.

The user input unit receives the input of an administrator. The user input unit may include one or more of various input devices capable of receiving the input of the administrator, for example, a keyboard, a mouse, a touchscreen, a voice recognizer, and the like. The administrator may input some information and/or data to change the care schedule for each of the plurality of patients through the user input unit.

The output unit outputs information to the administrator. The output unit may include one or more of various output devices including a display, a speaker, and the like. Specifically, the output unit may output care schedule data to the administrator.

Figure 14:
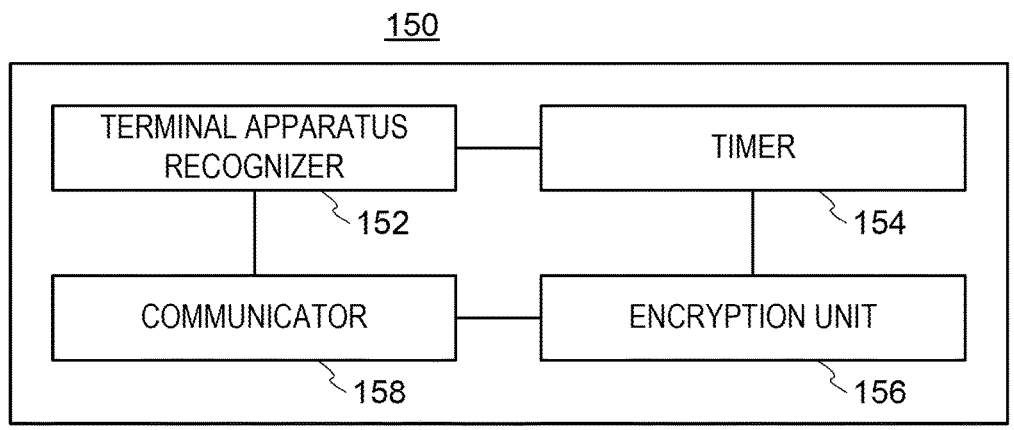
FIG. 14 illustrates a smart card according to an embodiment of the present disclosure.

FIG. 14 illustrates a smart card according to an embodiment of the present disclosure. The smart card 150 includes a terminal apparatus recognizer 152, an encryption unit 156, and a communicator 158, but embodiments are not limited thereto.

The terminal apparatus recognizer 152 recognizes the terminal apparatus 110 after tapping smart card 150 to the card recognizer or sliding the smart card 150 through the card recognizer.

The encryption unit 156 generates encrypted data including encrypted time information by encrypting, using a pre-stored encryption key, time information corresponding to a point in time when the terminal apparatus 110 is recognized by the terminal apparatus recognizer 152. The encrypted data may further include encrypted identification information and a hash value of the smart card 150.

The communicator 158 communicates with the terminal apparatus 110 through a local area network to transmit/receive data. The communicator 158 transmits the encrypted data generated by the encryption unit 156 to the terminal apparatus 110. In addition, while transmitting the encrypted data to the terminal apparatus 110, the communicator 158 may also transmit unencrypted identification information of the smart card 150 to the terminal apparatus 110.

The smart card 150 may further include a timer 154. The timer 154 determines a present time so as to acquire the time information on the point in time when the terminal apparatus 110 is recognized by the terminal apparatus recognizer 152.

In accordance with embodiments of the present disclosure, a system and method for managing a care service, and a terminal apparatus, a management server, and a smart card can accurately manage a time when a caregiver provides the care service to a patient, even when the terminal apparatus and the management server are not connected through a network.

In addition, the system and method for managing the care service, and the terminal apparatus, the management server, and the smart card for managing the care service can prevent the caregiver from falsifying the times related to the provision of care services.

In accordance with embodiments of the present disclosure, the elements of the terminal apparatus 110, the management server 130, the smart card 150 illustrated in FIGS. 12 to 14, respectively, refer to functional blocks. In each of the terminal apparatus 110, the management server 130, the smart card 150, the elements may be implemented with at least one processor, and operations of the elements may be controlled by program(s) stored in at least one memory.

In accordance with embodiments of the present disclosure, the foregoing methods may be implemented as code that can be read by a computer and stored on a non-transitory computer-readable medium. The computer-readable medium may include any type of recording device in which data that can be read by a computing system is stored. The computer-readable medium may be implemented as one or more of ROM, RAM, a CD-ROM, a magnetic tape, a floppy disk, an optical data storage device, and the like. The computer-readable recording medium may be distributed over network-coupled computer systems so that the computer-readable code may be stored and executed in a distributed fashion.

The broad teachings of the present disclosure can be implemented in a variety of forms. Therefore, while this disclosure includes particular examples, the true scope of the disclosure should not be so limited since other modifications will become apparent upon a study of the drawings, the specification, and the following claims.

What is claimed is:

1. A method for managing a care service by a terminal apparatus of a caregiver, the method comprising:
recognizing, using a card recognizer of the terminal apparatus, a smart card of a patient a first time when the caregiver starts a care service for the patient;
transmitting, to the smart card, first time information corresponding to a point in time when the terminal apparatus recognizes the smart card the first time;
receiving first encrypted data including encrypted first time information from the smart card and storing the first encrypted data, the encrypted first time information being generated at the smart card by encrypting the first time information using an encryption key pre-stored in the smart card; and transmitting the first encrypted data to a management server when the terminal apparatus connects to the management server, wherein the terminal apparatus has no decryption key and the management server has a decryption key corresponding to the encryption key, wherein the method further comprises:

recognizing, using the card recognizer, the smart card a second time when the caregiver ends the care service for the patient;

transmitting, to the smart card, second time information corresponding to a point in time when the terminal apparatus recognizes the smart card the second time;

receiving second encrypted data including encrypted second time information from the smart card, the encrypted second time information being generated by the smart card by encrypting the second time information using the encryption key; and transmitting the second encrypted data to the management server when the terminal apparatus connects to the management server, wherein the method further comprises determining a present time so as to acquire each of the first and second time information, wherein the management server stores a care service start time and a care service end time based on the first encrypted data and the second encrypted data, respectively, wherein the first and second time information are prevented from being modified by the caregiver, and wherein transmitting the encrypted data comprises:
when the terminal apparatus connects to the management server through the network, transmitting each of the first and second encrypted data to the management server; and
when the terminal apparatus does not connect to the management server through the network, storing each of the first and second encrypted data to transmit each of the stored first and second encrypted data when the terminal apparatus connects to the management server after a predetermined time elapses.

2. The method of claim 1, further comprising:
receiving identification information of the smart card from the smart card;
comparing the identification information of the smart card with identification information of smart cards of patients assigned to the caregiver; and
determining whether the patient is assigned to the caregiver based on a result of the comparison,
wherein transmitting the first encrypted data comprises transmitting the encrypted data to the management server when it is determined that the patient is assigned to the caregiver and when the terminal apparatus connects to the management server.

3. The method of claim 2, further comprising:
outputting information on the patients assigned to the caregiver when it is determined that the patient is not assigned to the caregiver.

4. The method of claim 2, further comprising:
outputting information on a care service to be provided to the patient when it is determined that the patient is assigned to the caregiver.

5. The method of claim 1, wherein the smart card generates the encrypted data using the encryption key, and the management server decrypts the encrypted data using the decryption key.

6. The method of claim 1, further comprising:
outputting an alarm message when the smart card is not recognized within a predetermined time interval from a visit reservation time for the patient.

7. The method of claim 1, further comprising:
receiving care schedule data from the management server; and
receiving a push message indicating a change of a care schedule, which corresponds to the care schedule data, from the management server when the care schedule is changed after the terminal apparatus has received the care schedule data.

8. The method of claim 1, further comprising:
receiving condition information of the patient; and
transmitting the condition information to the management server.

9. The method of claim 1, further comprising:
receiving biometric information of the caregiver; and
authenticating the caregiver using the biometric information.

10. A terminal apparatus of a caregiver, the terminal apparatus comprising:
a card recognizer configured to recognize a smart card of a patient;
a memory having stored therein instructions; and
a processor being controlled by the instructions and performing a method, the method comprising:
transmitting, to the smart card, first time information corresponding to a point in time when the terminal apparatus recognizes the smart card a first time, the smart card being first recognized when the caregiver starts a care service for the patient;
receiving first encrypted data including encrypted first time information from the smart card and storing the first encrypted data, the encrypted first time information being generated at the smart card by encrypting the first time information using an encryption key pre-stored in the smart card; and
transmitting the first encrypted data to a management server when the terminal connects to the management server,
wherein the terminal apparatus has no decryption key and the management server has a decryption key corresponding to the encryption key,
wherein, when the card recognizer recognizes the smart card a second time, the method further comprises:
transmitting, to the smart card, second time information corresponding to a point in time when the terminal apparatus recognizes the smart card the second time, the smart card being second recognized when the caregiver ends the care service for the patient;
receiving second encrypted data including encrypted second time information from the smart card, the encrypted second time information being generated at the smart card by encrypting the second time information using the encryption key; and
transmitting the second encrypted data to the management server when the terminal apparatus connects to the management server,
wherein the method further comprises determining a present time so as to acquire each of the first and second time information, wherein the management server stores a care service start time and a care service end time based on the first encrypted data and the second encrypted data, respectively, wherein the first and second time information are prevented from being modified by the caregiver, and wherein transmitting the encrypted data comprises:
when the terminal apparatus connects to the management server through the network, transmitting each of the first and second encrypted data to the management server; and
when the terminal apparatus does not connect to the management server through the network, storing each of the first and second encrypted data to transmit each of the stored first and second encrypted data when the terminal apparatus connects to the management server after a predetermined time elapses.

11. The terminal apparatus of claim 10, wherein the method further comprises:
receiving identification information of the smart card from the smart card;
comparing the identification information of the smart card with identification information of smart cards of patients assigned to the caregiver; and
determining whether the patient is assigned to the caregiver based on a result of the comparison,
wherein transmitting the encrypted data comprises transmitting the encrypted data to the management server when it is determined that the patient is assigned to the caregiver and when the terminal apparatus connects to the management server.

12. The terminal apparatus of claim 11, wherein the method further comprises:
outputting information on the patients assigned to the caregiver when it is determined that the patient is not assigned to the caregiver.

13. The terminal apparatus of claim 10, wherein the method further comprises:
receiving identification information of the smart card from the smart card; and
outputting information on a care service to be provided to a patient corresponding to the identification information of the smart card.

14. The terminal apparatus of claim 10, wherein the method further comprises:
outputting an alarm message when the smart card is not recognized within a predetermined time interval from a visit reservation time for the patient.

15. The terminal apparatus of claim 10, wherein the method further comprises:
receiving care schedule data from the management server; and
receiving a push message indicating a change of a care schedule corresponding to the care schedule data from the management server when the care schedule is changed after the care schedule data has been received.

16. The terminal apparatus of claim 10, wherein the method further comprises:
receiving condition information of the patient; and
transmitting the condition information to the management server.

17. The terminal apparatus of claim 10, wherein the method further comprises:
receiving biometric information of the caregiver; and
authenticating the caregiver using the biometric information.

18. A non-transitory computer readable medium having stored thereon a program that, when executed, causes a processor to perform a method for managing a care service by a terminal apparatus of a caregiver, the method comprising:
transmitting, to a smart card of a patient, first time information corresponding to a point in time when the terminal apparatus recognizes, using a card recognizer, the smart card a first time, the smart card being first recognized when the caregiver starts a care service for the patient;
receiving first encrypted data including encrypted first time information from the smart card and storing the first encrypted data, the encrypted first time information being generated at the smart card by encrypting the first time information using an encryption key prestored in the smart card; and
transmitting the first encrypted data to a management server when the terminal apparatus connects to the management server,
wherein the terminal apparatus has no decryption key and the management server has a decryption key corresponding to the encryption key,
wherein the method further comprises:
transmitting, to the smart card, second time information corresponding to a point in time when the terminal apparatus recognizes, using the card recognizer, the smart card a second time, the smart card being second recognized when the caregiver ends the care service for the patient;
receiving second encrypted data including encrypted second time information from the smart card, the encrypted second time information being generated by the smart card by encrypting the second time information using the encryption key; and
transmitting the second encrypted data to the management server when the terminal apparatus connects to the management server,
wherein the method further comprises determining a present time so as to acquire each of the first and second time information,
wherein the management server stores a care service start time and a care service end time based on the first encrypted data and the second encrypted data, respectively,
wherein the first and second time information are prevented from being modified by the caregiver, and
wherein transmitting the encrypted data comprises:
when the terminal apparatus connects to the management server through the network, transmitting each of the first and second encrypted data to the management server; and
when the terminal apparatus does not connect to the management server through the network, storing each of the first and second encrypted data to transmit each of the stored first and second encrypted data when the terminal apparatus connects to the management server after a predetermined time elapses.

* * * * *